United States Patent [19]

Snyder

[11] Patent Number: 5,064,646
[45] Date of Patent: Nov. 12, 1991

[54] NOVEL INFECTIOUS BURSAL DISEASE VIRUS

[75] Inventor: David B. Snyder, Seabrook, Md.

[73] Assignee: The University of Maryland, College Park, Md.

[21] Appl. No.: 227,311

[22] Filed: Aug. 2, 1988

[51] Int. Cl.$^5$ .......................... A61K 39/12; C12N 7/00
[52] U.S. Cl. ...................................... 424/89; 424/85.8; 424/86; 435/235.1; 435/236; 530/387
[58] Field of Search .......................... 424/89, 85.8, 86; 435/235.1, 236; 530/387

[56] References Cited

U.S. PATENT DOCUMENTS 4,530,831  7/1985  Lütticken et al. ..................... 424/89
4,824,668  4/1989  Melchior, Jr. et al. ............... 424/89

OTHER PUBLICATIONS

Fahey et al., "Antibody to the 32K Structural Protein of Infectious Bursal Disease Virus Neutralizes Viral Infectivity in Vitro and Confers Protection on Young Chickens", J. Gen. Virol., vol. 66, pp. 2693-2702, 1985.

Cho et al., "An Immunoperoxidase monoclonoal Antibody Stain for Rapid Diagnosis of Infectious Bursal Disease", Avian Diseases, vol. 31, pp. 538-545, 1987.

Primary Examiner—Garnette D. Draper
Assistant Examiner—Abdel A. Mohamed
Attorney, Agent, or Firm—Oblon, Spivak, McClelland, Maier & Neustadt

[57] ABSTRACT

A new virus not neutralized or bound by monoclonal antibodies which bind and neutralize all IBD vaccines of current art, and capable of inducing infectious bursal disease in poultry is identified, in essentially pure form. A test kit, and assay for the presence of the virus is disclosed, together with the vaccine incorporating the virus.

9 Claims, No Drawings

NOVEL INFECTIOUS BURSAL DISEASE VIRUS

FIELD OF THE INVENTION

This invention relates to the poultry industry, and in particular, infectious bursal disease, a known scourge of this industry. Specifically, a novel virus is identified, and methods of using this virus and information associated therewith are disclosed.

BACKGROUND OF THE PRIOR ART

Infectious bursal disease (IBD) has previously been identified as a significant economic drain in the poultry industry. This disease, which strikes chiefly at the chicken industry, is caused by virulent field viruses which cause a highly contagious, immunosuprive disease condition. This condition, of course, exacerbates other infections in the chicken population. The disease is noted for its impact on young chickens, and is characterized by lesions in the lymphoidal follicles of the bursa of Fabricius.

In U.S. Patent Application Ser. No. 07/061,083, filed June 12, 1987, the inventor herein, and others, reported the development of two monoclonal antibodies sensitive to, and capable of neutralizing, all known viruses identified as inducing IBD. The entire disclosure of that application is incorporated herein by reference. Indeed, that application, which is still pending, addresses the monoclonal antibodies, particularly those identified as R63 and B69, expressed by hybridomal cell lines deposited in June, 1988 at the ATCC in Rockville, Maryland, USA under ATCC HB-9437 and HB-9490, which continue to prove their value as neutralizing monoclonal antibodies, comprising a passive vaccine against known strains of viruses inducing IBD.

Nonetheless, recent history in the poultry industry, particularly that along the eastern coast of the United States, reflects an increasingly large number of reports of outbreaks of infectious bursal disease, which are not fully prevented by any of the known vaccines, including those prepared from the monoclonal antibodies discussed above. Due to the severe economic strain placed on the poultry industry by these uncontrolled outbreaks, a significant degree of investigation of the cause of the outbreaks, and the reason for the failure of known vaccines to prevent such outbreaks, has been undertaken. No fault has been detected in the preparation of the vaccines, or their administration. Nonetheless, unchecked outbreaks continue to occur.

Accordingly, it remains a persistent problem of the prior art to determine the cause of these outbreaks of infectious bursal disease which are resistant to any of the known vaccines, and determine a method of preventing further such outbreaks.

SUMMARY OF THE INVENTION

It has now been discovered that a major virus responsible for infectious bursal disease in poultry along the east coast of the USA is a newly identified, varient strain with altered recognition sites, such that neither of the previously developed monoclonal antibodies are capable of neutralizing or binding the virus. However, these monoclonal antibodies do neutralize and react with all known IBD vaccines of the current art. The virus has been isolated in essentially pure form and can be identified by the failure of monoclonal antibody R63 and B69 to bind thereto, while another common non-neutralizing antibody as well as standard polyclonal antisera available from the USDA will bind thereto in positive fashion.

The new virus may be used in killed form as killed vaccines inducing antibodies resistant to the new virus, and may be used in attenuated form or otherwise genetically altered to prepare either a live or killed virus vaccine.

DETAILED DESCRIPTION OF THE INVENTION

As noted above, the new virus, drawn from at least 116 novel isolates, taken from the east and Southeastern United States are not neutralized by any of the monoclonal antibodies previously developed and described. Thus, identification of the presence of the new virus cannot be achieved through normal measures. However, by a combination of negative and positive testing, the presence of the virus and isolation of the virus can be achieved.

In particular, the monoclonal antibody designated R63, which neutralizes all previously identified serotype one IBD virus strains and at least one serotype two gave negative results in an antigen capture-ELISA when reacted with the homogenized bursas drawn from chickens which yielded the twenty-three isolates. The same results were observed with MCA-B69, selective for the D78 virus strain and certain classic viruses of an earlier art, once thought to be the prevalent strain in the United States. At the same time, another MCA designated B29, expressed by a hybridomal cell line deposited at the ATCC under accession number MB 9746, pursuant to Budapest Treaty conditions, which does not neutralize the virus, nevertheless binds to it, as well as to all known existing virus vaccines. Additionally, the polyclonal IBDV antisera used as a standard, and available from the USDA's national veterinary services Laboratory in Ames, Iowa under designation ADU8701, binds, in the antigen capture ELISA, to the novel vaccine. Other non-neutralizing antibodies can be identified which bind to the virus, and can be directly produced as conventional monoclonal antibodies. The invention is not limited to any given positive test factor. Since the overall size of the virus, in comparison to any available neutralization site is quite large, there will be a large potential field of such positive test factors and polyclonal antisera.

Thus, the presence of the virus can currently be best determined by negative testing in an antigen capture-ELISA for R63 and B69, and positive testing with either B29 or the polyclonal antisera. It should be noted, however, that morphological or symptomatic verification of the presence of an IBD virus, coupled with a failure of the R63 MCA to bind to an antigen sample, is clear evidence of the presence of the virus.

IDENTIFICATION OF THE VIRUS PRESENCE

To originally identify the presence of the new virus, 116 chicken populations were sampled, bursas were obtained from 116 distinct flocks on the Delmarva Peninsula and the Southeastern U.S. poultry rearing areas. Bursas from the 116 chicken populations were homogenized by placing one bursa in one ml of SGPA-EDTA buffer and grinding the mixture with a mortar and pestle until fluid-like consistency was obtained. This material was clarified by low speed centrifugation, and the supernatants were analyzed by an AC-ELISA.

In this assay, 96-well Immulon 1 plates (obtained from Dynatech, of Virginia) were coated with 0.1 ml of two ug/ml of protein A from Staphlycoccus aureus in a coating buffer. After 18 hours at 4° C, the plates were dumped. 1/10 Dilutions of acid supernatents collected from hybridoma cultures secreting the R63 and B69 IBD virus specific MCAs were added in the phosphate buffered saline which contained TWEEN 20 and 2% non-fat dried powdered milk, in alternating fashion. After a 24 hours reaction at 4° C., the plates were tapped dry and blocked for 30 minutes at room temperature. After blocking, the plates were emptied and tapped dry. 0.1 ml of serial dilutions of each sample of the homogenized bursal suspensions were added to the coated plates, and after incubation, the plates were emptied, tapped dry and washed three times for three minutes with PBS-T. Then, each well received 0.1 ml of a biotin labelled R63 MCA conjugate, which was diluted in PBS-T +NFDM. After an hour of incubation, the plates were again emptied and washed. Subsequently, 0.1 ml of a streptavidin-horseradish peroxidase conjugated was added to each well. After one hour of incubation the plates were again emptied and washed. This was followed by the addition of a TMB substrate. After a brief incubation period, the tests were read at 650 nm with the aid of an automated spectrophotometer. Thus, the biotinylated R63 MCA was used to signal for positive reactions between the virus and R63 and B69 wells, while a similar AC-ELISA was performed with a polyclonal anti-IBDV sera was used to signal the B29 catches. Alternatively, biotinylated B29 could be used to the same effect. Further, any form of labeling of R63, B69, B29, polyclonal may be used.

All 116 strains showed negative for reactivity with R63 and B69, but were highly positive for the B29 MCA, which combines in a non-neutralizing fashion.

As R63 is a neutralizing antibody for all previously identified IBD viruses, an assay employing only R63 as the positive non-neutralizing assay is adequate. The added use of B69 gives a higher confidence level, and can be used to further define and separate IBDV strains of the prior art.

CONFIRMATION OF THE PURITY AND VIRULENCE OF THE VIRUS

Samples from five of the identified isolated strains, which virus is expressed by the deposits at the Institute Pasteur 1/25 Rue duDr. Roux, 75724 Paris, Cedex 15, France in July, 1988 pursuant to Budapest Treaty conditions under accession numbers i.-792 and i.-793 were pooled, and reacted with the R63 MCA, and innoculated into SPF chickens. Five days after innoculation, these chickens, and non-innoculated chicken were necropsied. Those birds innoculated with the collected pool, referred to as NegaVac (NV) showed lesions consistent only with infectious bursal disease.

For certainty, antisera from the birds was taken at 11 days past innoculation, and was tested by indirect ELISA and showed seriologic conversion to IBDV, but to no other related poultry diseases. Bursal samples from these birds were homogenized and passed a second time in the presence of R63 and B69 with identical results. In both passages, on a scale of 0-9, reactivity with the B29 MCA was at level 9, and reactivity with B69 and R63 was at level 0. Thus, a pure preparation of a previously unidentified virus, not related to any known vaccine at the R63 and B69 neutralization sites, prepared from virus or otherwise, was identified. Preparation of additional monoclonal antibodies, protein information, and RNA analysis, is underway. This information will provide the necessary base for the preparation of vaccines based on neutralizing, but non-toxic, recombinant virus-like proteins.

Until such "designed" vaccines become available, any of the isolated virus preparations each given the designation $GLS_n$ (n=1-116 currently) can be used, in killed form, for the preparation of conventional killed vaccines, which do confer immunity against the new virus. The GLS strains may be prepared into a vaccine through common methods, which are not per se a part of this invention among the most prominent of which are heat killing and chemical killing, which preserves the essential form of the vaccine to enable the preparation, by the innoculated bird, of protective NV antibodies while rendering it non-virulent. Alternatively, there are known methods of attenuating viruses, including serial passage, cloning of the virus deleting sequences of nucleic acids and site-directed mutagenesis, which will allow the preparation of a live non-virulent virus vaccine. The vaccines may be prepared by simple incorporation of the selected virus derivative and suspending or mixing it in a carrier. Appropriate dosage values can be determined through routine trial and error techniques, sampling for antibody titer.

As important as the preparation of the new vaccine is, there is now provided a method by which the presence of the virus can be identified in a given poultry population, by a relatively quick and efficient ELISA assay, which, if reaction to R63 alone, or R63 and B69 together is negative, while the reaction to a polyclonal vaccine or B29, is positive, then the presence of the virus is confirmed. B29 is expressed by a hybridomal cell line which has been deposited, under Budapest Treaty terms at the ATCC, under accession number HB 9746.

As of the filing of this application, at least 333 flocks had been so tested. Of these, 116 tested negatively against the R63 monoclonal antibody alone, or R63 and B69, taken together while positively for the B29 MCA. Thus, the new virus appears to be a dominant and growing factor in the causation of infectious bursal disease in chickens.

It is uncertain, as of the filing date of this application, whether the newly identified virus is a subtype or constitutes a new IBDV serotype, although there is considerable evidence that it is a serotype One subtype. In any event, identification of the presence of the virus and the preparation of a vaccine therefrom is achieved in the same manner whether strain or serotype, and accordingly, the invention is not limited thereby.

Obviously, numerous modifications and variations of the present invention are possible in light of the above teachings. It is therefore to be understood that within the scope of the appended claims, the invention may be alternatively described or practiced otherwise than as specifically described herein.

What is claimed as new and desired to be secured by Letters Patent of the United States is:

1. A substantially pure preparation of virus which induces infectious bursal disease (IBD) in poultry, to which monoclonal antibody R63 will not bind when said monoclonal antibody and virus are contacted in an antigen -captured-enzyme-linked immunoassay said virus having IBD inducing characteristics and monoclonal antibody binding characteristics of the virus deposited under the C.N.C.M. No-I-792 and I-793.

2. A substantially pure preparation, consisting essentially of a virus which induces infectious bursal disease in poultry to which monoclonal antibody R63 will not bind when contacted with said virus in an antigen-captured-enzyme-linked immunoassay, and to which a test factor selected from the group consisting from polyclonal antisera USDA ADV 8071 and monoclonal antibody B29 will bind, when contacted with said virus in an antigen-capture-enzyme-linked immunoassay said virus having IBD inducing characteristics and monoclonal antibody binding characteristics of the virus deposited under the C.N.C.M. No. I-792 and I-793.

3. The preparation of claim 1, wherein said virus is suspended in either a non-immunogenic medium or an immunogenic medium.

4. The preparation of claim 1, wherein monoclonal antibody B69 will not bind to said virus when contacted with said virus in an antigen-captured-enzyme-linked immunoassay.

5. A vaccine for the prevention of infectious bursal disease in poultry, comprising: a virus which induces infectious bursal disease in poultry, to which virus monoclonal antibody R63 will not bind, when contacted with said virus in an antigen-capture-enzyme linked imunoassay, and a pharmacologically acceptable carrier therefor said virus having IBD inducing characteristics and monoclonal antibody binding characteristics of the virus deposited under the C.N.C.M. No. I-792 and I-793.

6. The vaccine of claim 5, wherein said virus is in a killed form.

7. The vaccine of claim 5, wherein said virus is in a live but attenuated form.

8. The vaccine of claim 5, further comprising monoclonal antibody R63.

9. The vaccine of claim 5, further comprising monoclonal antibody B69.

* * * * *